US009603784B2

(12) United States Patent
Shimizu et al.

(10) Patent No.: US 9,603,784 B2
(45) Date of Patent: Mar. 28, 2017

(54) PROCESS FOR TREATING SOL-GEL CAPSULES

(75) Inventors: Kaiman Shimizu, Roth (DE); Yukitaka Watanabe, Iwaki (JP); Yuichi Kubota, Yokohama (JP); Fumiko Sasaki, Iwaki (JP); Keisuke Kawagoe, Yokohama (JP); Gabriele Witte, Buettelborn (DE); Frank Pfluecker, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 878 days.

(21) Appl. No.: 13/818,307

(22) PCT Filed: Sep. 1, 2011

(86) PCT No.: PCT/EP2011/004420
§ 371 (c)(1),
(2), (4) Date: Feb. 22, 2013

(87) PCT Pub. No.: WO2012/041438
PCT Pub. Date: Apr. 5, 2012

(65) Prior Publication Data
US 2013/0156834 A1 Jun. 20, 2013

(30) Foreign Application Priority Data

Sep. 30, 2010 (EP) .................................. 10012005
Oct. 23, 2010 (EP) .................................. 10013909

(51) Int. Cl.
| A61K 8/11 | (2006.01) |
| A61Q 17/04 | (2006.01) |
| B01J 13/18 | (2006.01) |
| B01J 13/20 | (2006.01) |
| B82Y 30/00 | (2011.01) |
| C09C 1/30 | (2006.01) |
| C09C 3/06 | (2006.01) |
| A61K 9/00 | (2006.01) |
| A61K 47/10 | (2017.01) |

(52) U.S. Cl.
CPC .............. *A61K 8/11* (2013.01); *A61K 9/0014* (2013.01); *A61K 47/10* (2013.01); *A61Q 17/04* (2013.01); *B01J 13/18* (2013.01); *B01J 13/20* (2013.01); *B82Y 30/00* (2013.01); *C09C 1/3054* (2013.01); *C09C 3/063* (2013.01); *A61K 2800/412* (2013.01); *C01P 2002/84* (2013.01); *C01P 2004/03* (2013.01); *C01P 2004/61* (2013.01); *C01P 2004/62* (2013.01); *C01P 2004/64* (2013.01); *C01P 2004/86* (2013.01); *C01P 2006/60* (2013.01)

(58) Field of Classification Search
CPC ........ A61K 8/11; A61K 9/0014; A61K 47/10; A61K 2800/412; A61Q 17/04; B01J 13/18; B01J 13/20
See application file for complete search history.

(56) References Cited

U.S. PATENT DOCUMENTS

| 5,512,094 | A | 4/1996 | Linton |
| 6,238,649 | B1 | 5/2001 | Habeck et al. |
| 6,238,650 | B1 | 5/2001 | Lapidot et al. |
| 6,242,099 | B1 | 6/2001 | Grandmontagne et al. |
| 6,303,149 | B1 | 10/2001 | Magdassi et al. |
| 6,436,375 | B1 | 8/2002 | Lapidot et al. |
| 6,545,174 | B2 | 4/2003 | Habeck et al. |
| 6,648,958 | B2 * | 11/2003 | Anselmann ........... C09C 1/3054 106/436 |
| 2002/0016310 | A1 | 2/2002 | Habeck et al. |
| 2004/0175335 | A1 | 9/2004 | Pflucker et al. |
| 2004/0220137 | A1 | 11/2004 | Sauermann |
| 2005/0037087 | A1 | 2/2005 | Lapidot et al. |
| 2008/0317795 | A1 * | 12/2008 | Traynor et al. ................ 424/401 |
| 2009/0081262 | A1 | 3/2009 | Toledano et al. |
| 2009/0297852 | A1 | 12/2009 | Frahm et al. |
| 2009/0304756 | A1 | 12/2009 | Dahne et al. |
| 2010/0016443 | A1 | 1/2010 | Toledano et al. |
| 2012/0321685 | A1 | 12/2012 | Lapidot et al. |

FOREIGN PATENT DOCUMENTS

| CN | 101555401 A | 10/2009 |
| DE | 10133202 A1 | 1/2003 |
| DE | 102008026300 A1 | 12/2009 |
| EP | 0487404 A1 | 5/1992 |
| EP | 0916335 A2 | 5/1999 |
| EP | 1115796 B1 | 1/2003 |
| JP | 07323668 A | 12/1995 |
| JP | 09169626 A | 6/1997 |
| JP | 1023851 A | 1/1998 |

(Continued)

OTHER PUBLICATIONS

Seok et al., Encapsulation of Water-Soluble Dye in Sphereical Sol-Gel Silica Matricies, Jul. 2003, Journal of Sol-Gel Science and Technology, vol. 27 iss. 3, pp. 355-361.*
English language translation of Japanese Office Action for corresponding JP Application No. 2013-530601; dated Apr. 27, 2015.
English language Abstract for corresponding JP Application No. 2009-503056; published Jan. 29, 2009.
English language Abstract for corresponding JP Application No. 2010-517997; published May 27, 2010.
English language Abstract for corresponding JP Application No. 09169626; published Jun. 30, 1997.
English language Abstract for corresponding JP Application No. 11196324; published Jul. 21, 1999.

(Continued)

*Primary Examiner* — Ali Soroush
(74) *Attorney, Agent, or Firm* — Millen White Zelano and Branigan, PC; Csaba Henter; Anthony Zelano

(57) ABSTRACT

The present invention relates to a process for treating sol-gel capsules comprising a cosmetic or pharmaceutical active material with an inorganic material, as well as sol-gel capsules produced by a process according to the present invention and formulations comprising such sol-gel capsules.

22 Claims, 12 Drawing Sheets

(56) References Cited

FOREIGN PATENT DOCUMENTS

Figure 1:
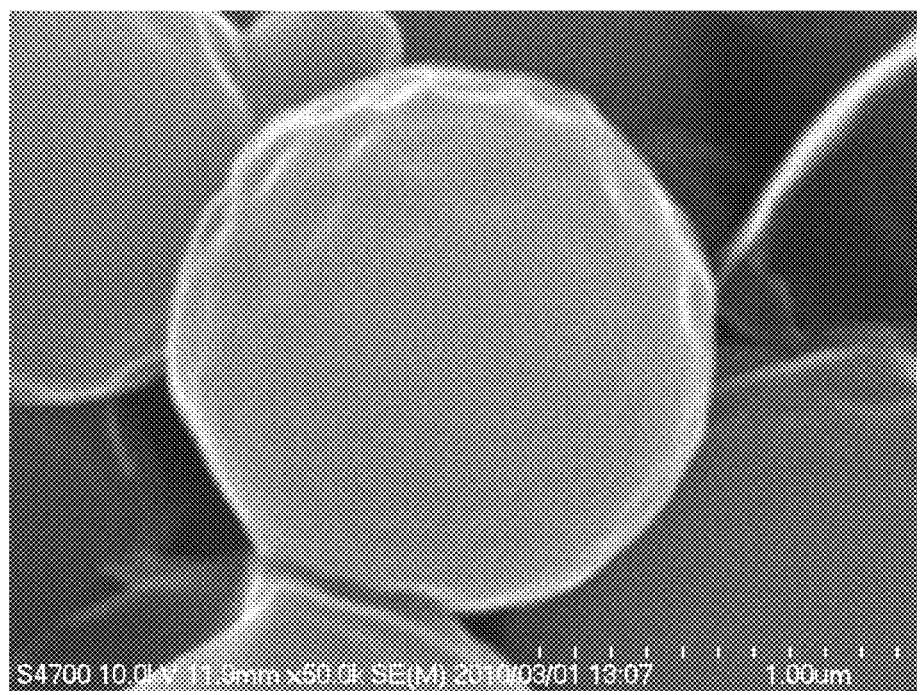

| | | | |
|---|---|---|---|
| JP | 11196324 | A | 7/1999 |
| JP | 2005504750 | A | 2/2005 |
| JP | 2005526025 | A | 9/2005 |
| JP | 2009503056 | A | 1/2009 |
| JP | 2009507592 | A | 2/2009 |
| JP | 2009173934 | A | 8/2009 |
| JP | 2010517997 | A | 5/2010 |
| WO | 9304665 | A1 | 3/1993 |
| WO | 0009652 | A2 | 2/2000 |
| WO | WO-00/09652 | * | 2/2000 |
| WO | 0015720 | A1 | 3/2000 |
| WO | 0071084 | A1 | 11/2000 |
| WO | 0072806 | A2 | 12/2000 |
| WO | 0180823 | A2 | 11/2001 |
| WO | 03007906 | A1 | 1/2003 |
| WO | 03011239 | A2 | 2/2003 |
| WO | 03039510 | A1 | 5/2003 |
| WO | 03066209 | A1 | 8/2003 |
| WO | 2007015243 | A2 | 2/2007 |
| WO | 2007031345 | A2 | 3/2007 |
| WO | 2008093347 | A2 | 8/2008 |

OTHER PUBLICATIONS

English language Abstract for corresponding JP Application No. 2005-504750; published Feb. 17, 2005.
English language Abstract for corresponding JP Application No. 2009-507592; published Feb. 26, 2009.
English language Abstract for corresponding JP Application No. 2009-173934; published Aug. 6, 2009.
English language Abstract for corresponding JP Application No. 07323668; published Dec. 12, 1995.
English language Abstract for corresponding JP Application No. 1023851; published Jan. 27, 1998.
English language Abstract for corresponding JP Application No. 2005-526025; published Sep. 2, 2005.
Katarzyna Lemanska et al. "The Influence of pH on Antioxidant properties and the mechanism of antioxidant action of Hydroxyflavones" Elsevier, Free Radical Biology & Medicine, vol. 31, No. 7, pp. 869-881 (2001).
Catherine A. Rice-Evans et al. "Antioxidant Properties of Phenolic Compounds" Elsevier Science Ltd., Trends in Plant Science, (Apr. 1997) vol. 2, No. 4, pp. 152-159.
Katarzyna Lemanska et al. "Effect of Substitution Pattern on Teac Antioxidant Activity of Mono- and Dihydroxyflavones" Current Topics in Biophysics (2000), 24 (2), pp. 101-108.
Mitchell L Schlossman "Treated Pigments, New Ways to Impart Color on the Skin" Cosmetics & Toiletries (Feb. 1990), vol. 105, pp. 53-64.
Abstract of EP0487404A1 dated May 27, 1992.
Abstract of WO9304665A1 dated Mar. 18, 1993.
Abstract of EP1115796B1 dated Jan. 15, 2003.
Abstract of CN101555401A dated Oct. 14, 2009.
Abstract of WO0015720A1 dated Mar. 23, 2000.

* cited by examiner

PROCESS FOR TREATING SOL-GEL CAPSULES

The present invention relates to a process for treating sol-gel capsules comprising a cosmetic or pharmaceutical active material with an inorganic material, as well as sol-gel capsules produced by a process according to the present invention and formulations comprising such sol-gel capsules.

A suntan of the skin to whatever degree is regarded in today's society as attractive and as an expression of vigour and sportiness. As well as this desired effect of the sun on the skin, a number of undesired secondary effects arise, such as sunburn or premature skin ageing and the development of wrinkles.

It is generally known that the ultraviolet part of sunlight has a harmful effect on the skin. While rays having a wavelength smaller than 290 nm (so-called UVC region) are absorbed by the ozone layer in the earth's atmosphere, rays in the range between 290 nm and 320 nm, the so-called UVB region, cause erythema, simple sunburn or even various degrees of burning.

It has also been shown that rays in the range between about 320 nm and 400 nm (UVA region) result in damage to the elastic and collagenic fibres of the connective tissue, which causes the skin to age prematurely. Furthermore, these rays are the cause of numerous phototoxic and photoallergic reactions. The harmful influence of UVB radiation may be augmented by UVA radiation. UVA radiation may furthermore cause skin damage by damaging the skin's own keratin or elastin. This reduces elasticity and water storage capacity of the skin, i.e. the skin becomes less supple and tends to form wrinkles. The strikingly high incidence of skin cancer in localities of strong sunlight shows that damage to erbin formations in the cells is apparently also caused by sunlight, especially by UVA radiation.

Therefore, a number of performance UV filters have been developed which, applied to the skin in the form of creams, lotions or gels, can effectively delay the development of sunburn even when the incidence of solar rays is relatively high. Known UV filters or sun protection agents thus act by absorbing certain regions of sunlight, meaning that this radiation cannot penetrate into deeper layers of the skin.

Depending on the position of their absorption maxima, UV absorbers for cosmetic and dermatological compositions are divided into UV-A and UV-B filters. Numerous compounds are known for protection against UVB radiation, mostly derivatives of 3-benzylidenecamphor (for example Eusolex® 6300), of 4-aminobenzoic acid, of cinnamic acid, of salicylic acid, of benzophenone and also of 2-phenylbenzimidazole. For protection against UVA radiation, use is frequently made of dibenzoylmethane derivatives, such as, for example, 4-(tert-butyl)-4'-methoxydibenzoylmethane (Eusolex® 9020) or 4-isopropyl-dibenzoylmethane (Eusolex® 8020).

In literature, the skin penetration by organic UV filters and the associated irritation potential on direct application to the human skin is repeatedly discussed. Therefore, many efforts have been performed in order to encapsulate the corresponding substances preventing direct skin contact.

Suitable capsules here can have walls of inorganic or organic polymers. For example, U.S. Pat. No. 6,242,099 B1 describes the production of capsules having walls of chitin, chitin derivatives or polyhydroxylated polyamines. Inorganic capsules may have walls which can be obtained by a sol-gel process, as described in the applications WO 00/09652 A2, WO 00/72806 A2, WO 00/71084 A1 and WO 03/39510 A1, e.g. walls built up from silica gel (silica; undefined silicon oxide hydroxide).

Silica obtained by a sol-gel process exhibits a porous structure. This may cause weakness against physical stress. Especially the preparation of a dry powder of UV filter capsules is complicated because of the high temperatures and the high mechanical stress applied during preparation. In order to facilitate the preparation of a powder of UV filter capsules very dense capsule walls are desirable.

Inorganic UV absorbers such as nanoparticulate $TiO_2$ are as well widely used in cosmetic applications.

These inorganic $TiO_2$ nanoparticles exhibit good UV absorbing properties. However, currently, nanopariticulate substances are often discussed to be harmful for human life. It is therefore desirable to provide $TiO_2$ in a non nanoparticulate form.

The object of the present invention was therefore to provide a process for treating sol-gel capsules with an inorganic material in order to obtain capsules with denser capsule walls and/or in order to obtain capsules exhibiting hybrid capsule walls.

WO 03/066209 A1 describes a process for encapsulating a lipophilic cosmetic, chemical, biological or pharmaceutical active material composition, wherein the microcapsules are post-treated with a water-reactive metal alkoxy or acyloxy compound, preferably with an alkoxysilane. This water-reactive metal alkoxy or acyloxy compound can for example harden the shell of the microcapsules and/or make them more impermeable.

CN 101555401A discloses the use of $TiCl_4$ and $Na_2SiO_3$ in order to treat the shells of microcapsules of organic phase change materials for energy storage with $TiO_2$ and $SiO_2$, respectively.

DE 10 2008 026 300 A1 describes a process for coating solid inorganic $TiO_2$ particles with $SiO_2$ using a sodium silicate solution.

In EP 1115796 B1 a process for coating spherical solid $SiO_2$ particles with $TiO_2$ followed by $SiO_2$ coating is disclosed. In this process an aqueous titanium salt solution and a sodium water glass solution is used, respectively.

A first aspect of the present invention is therefore a process for treating sol-gel capsules comprising an encpasulated cosmetic or pharmaceutical active material with an inorganic material, characterized in that the treatment comprises the following steps:

a) providing a suspension of sol-gel capsules, b) addition of one or more water-soluble inorganic precursor compounds, c) precipitation of the inorganic material onto the capsules' surfaces, d) optionally repeating steps b) and c) one or more times, and e) optionally drying the treated sol-gel capsules.

According to the present invention the term "treating" refers to further modifying the surfaces of the individual sol-gel capsules. Typically, this treatment is accomplished after the production of the sol-gel capsules, i.e. it is a post-treatment process.

In step a) a suspension of sol-gel capsules is provided. This suspension typically comprises sol-gel capsules suspended in water.

According to the present invention the sol-gel capsules are core-shell-capsules comprising a core of a cosmetic or pharmaceutical active material and a shell. The capsule shell (or "capsule wall") encapsulates the capsule's core, i.e. the cosmetic or pharmaceutical active material.

These capsule walls can be obtained by a sol-gel process, as for example described in the patent applications WO 00/09652 A2, WO 00/72806 A2, WO 00/71084 A1 and WO 03/39510 A1 or WO 03/066209 A1.

Preferably, the sol-gel capsules are silica capsules, i.e. capsules whose walls are made of silica gel (synonyms: silica, amorphous silicon oxide hydroxide). The preparation of corresponding capsules is known to the person skilled in the art, for example, from the above cited patent applications, the contents of which also expressly belonging to the subject-matter of the present application.

The process preferably used for the production of the sol-gel capsules provided in step a) is carried out in three steps:

in step a1), an oil-in-water emulsion of a hydrophobic solution comprising the sol-gel precursor and at least one cosmetic or pharmaceutical active material is prepared in an aqueous solution, in step b1), the emulsion from step a1) is mixed with another aqueous solution in order to accelerate the condensation polymerisation reaction, optionally in step c1) reaction products are separated off from the sol-gel precursor, and the sol-gel capsules are isolated.

After an appropriate reaction time, in which the mixture can also be warmed or cooled or the pH can also be modified, the capsules formed can be isolated in step c1) by means which are familiar to the person skilled in the art. For example, they can be centrifuged or filtered. A possible way of isolation is spray drying.

However, preference is given to a suspension of sol-gel capsules since in step a) of the treating process a suspension is employed.

The hydrophobic solution from step a1) and also the aqueous solutions from steps a1) and b1) may comprise surfactants and/or other additives which may improve this process and/or the product.

The sol-gel precursor can be a metal or semi-metal alkoxide monomer, a metal ester, semi-metal ester or a partially hydrolysed and partially condensed polymer, or a mixture thereof.

Suitable and preferred sol-gel precursors are also compounds of the formula $M(R)_n(P)_m$, in which M denotes a metal or semi-metal, preferably Si, R denotes a hydrolysable substituent, and n denotes an integer from 2 to 4, P denotes an unpolymerisable substituent, and m denotes an integer from 0 to 4, or a partially hydrolysed or partially condensed polymer thereof, or any mixture thereof.

The process for the production of sol-gel capsules described above is particularly preferably carried out using tetraethyl orthosilicate or a partially hydrolysed or partially condensed polymer thereof, or a mixture thereof. Tetraethyl orthosilicate is very particularly preferably employed as sol-gel precursor.

A further possible process which can be employed according to the present invention in order to obtain suitable sol-gel capsules is for example disclosed in WO 03/066209 A1. In this process a water reactive silicon compound comprising tetraalkoxysilane is added to an aqueous emulsion of the active material having a positive zeta-potential and the tetraalkoxysilane polymerises at the interface of the droplets in the emulsion forming the capsules.

In general, the encapsulation gives rise to many advantages, e.g. the hydrophilicity of the capsule wall can be adjusted independently of the solubility of the cosmetic or pharmaceutical active material. Thus, it is also possible to incorporate hydrophobic substances into purely aqueous formulations. Furthermore, the skin penetration by the active material and the possibly associated irritation potential is suppressed. Problems arising due to the interaction of individual formulation constituents with one another, such as crystallisation processes, precipitation and agglomerate formation, can be avoided if the substances are encapsulated separately.

The minimal particle size of the capsules depends on necessary size to prevent penetration of the skin. On the other side, the maximum particle size is limited by the application needs. It is advantageous here for the capsules to be sufficiently small that they cannot be seen with the naked eye. Preferred capsules have a average particle size in the range from about 10 nm up to about 10000 nm, preferably up to 5000 nm and most preferred up to 2000 nm.

The encapsulated cosmetic or pharmaceutical active material is typically a liquid at the time it is emulsified in step a1). Any cosmetic or pharmaceutical active material can be used.

Preferably, the cosmetic or pharmaceutical active material comprises one or more UV filters.

In principle, all known UV filters are suitable for encapsulation. Particular preference is given to UV filters whose physiological acceptability has already been demonstrated. Both for UVA and UVB filters, there are many proven substances which are known from the specialist literature.

The capsules may of course also comprise other sunscreen filters which are effective in the UV-A region and/or UV-B region and/or IR and/or VIS region (absorbers). These filters can be selected, in particular, from cinnamic acid derivatives, salicylic acid derivatives, camphor derivatives, triazine derivatives, β,β-diphenyl acrylate derivatives, p-aminobenzoic acid derivatives and polymeric filters and silicone filters, which are described in the application WO 93/04665. Further examples of organic filters are indicated in patent application EP-A 0 487 404.

Examples for suitable UV filters are benzylidenecamphor derivatives, such as 3-(4'-methylbenzylidene)-dl-camphor (e.g. Eusolex® 6300 sold by Merck), 3-benzylidenecamphor (e.g. Mexoryl® SD sold by Chimex), polymers of N-{(2 and 4)-[(2-oxoborn-3-ylidene)methyl] benzyl}-acrylamide (e.g. Mexoryl® SW), N,N,N-trimethyl-4-(2-oxoborn-3-ylidenemethyl)anilinium methylsulfate (e.g. Mexoryl® SK) or (2-oxoborn-3-ylidene)toluene-4-sulfonic acid (e.g. Mexoryl® SL sold by Chimex), camphor benzalkonium methosulfate (e.g. Mexoryl SO sold by Chimex), terephthalylidenedicamphorsulfonic acid (e.g. Mexoryl SX sold by Chimex), benzoyl- or dibenzoylmethanes, such as 1-(4-tert-butylphenyl)-3-(4-methoxyphenyl)propane-1,3-dione (e.g. Eusolex® 9020) or 4-isopropyldibenzoylmethane (e.g. Eusolex® 8020), benzophenones, such as 2-hydroxy-4-methoxybenzophenone (e.g. Eusolex® 4360) or 2-hydroxy-4-methoxybenzophenone-5-sulfonic acid and its sodium salt (e.g. Uvinul® MS-40), benzophenone-1 (e.g. Uvinul 400), benzophenone-2 (e.g. Uvinul D50), benzophenone-3 or oxybenzone (e.g. Uvinul M40), benzophenone-9 (e.g. Uvinul DS-49 sold by BASF), benzophenone-5, benzophenone-6 (e.g. Helisorb 11 sold by Norquay), benzophenone-8 (e.g. SpectraSorb UV-24 sold by American Cyanamid),
benzophenone-12,
4,4-diarylbutadienes as described in EP-A-0 916 335,
methoxycinnamic acid esters, such as
  octyl methoxycinnamate (for example Eusolex 2292),
  isopentyl 4-methoxycinnamate, for example as a mixture of the isomers (for example Neo Heliopan® E 1000),
salicylate derivatives, such as
  2-ethylhexyl salicylate (for example Neo Heliopan OS, sold by Symrise),
  4-isopropylbenzyl salicylate (for example Megasol®),
  3,3,5-trimethylcyclohexyl salicylate (Homosalate, e.g. Eusolex® HMS, sold by Merck KGaA),
  dipropylene glycol salicylate (e.g. Dipsal sold by Scher),
  TEA salicylate (e.g. Neo Heliopan TS sold by Symrise).
4-aminobenzoic acid and derivatives, such as
  4-aminobenzoic acid,
  2-ethylhexyl 4-(dimethylamino)benzoate (for example Eusolex® 6007),
  ethoxylated ethyl 4-aminobenzoate (for example Uvinul® P25),
and further substances, such as 2-phenylbenzimidazole-5-sulfonic acid, and its potassium, sodium and triethanolamine salts (e.g. Eusolex® 232), 3,3'-(1,4-phenylenedimethylene)-bis(7,7-dimethyl-2-oxobicyclo[2.2.1]hept-1-ylmethanesulfonic acid and its salts (e.g. Mexoryl® SX), 2,4,6-trianilino-(p-carbo-2'-ethylhexyl-1'-oxy)-1,3,5-triazine (e.g. Uvinul® T 150 sold by BASF) and 2-(4-Diethylamino-2-hydroxy-benzoyl)-benzoic acid hexyl ester (e.g. Uvinul® A Plus, BASF), diphenylacrylates, e.g. 2-ethylhexyl-2-cyano-3,3-diphenylacrylate (e.g. Eusolex® OCR, sold by Merck KGaA), Etocrylene (e.g. Uvinul N35 sold by BASF).

Further suitable UV filters are, for example,
  2-(2H-benzotriazol-2-yl)-4-methyl-6-(2-methyl-3-(1,3,3,3-tetramethyl-1-(trimethylsilyloxy)disiloxanyl)propyl) phenol (for example Silatrizole® sold by Rhodia Chimie),
  2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB sold by Sigma 3V),
  α-(trimethylsilyl)-ω-[trimethylsilyl)oxy]poly[oxy(dimethyl [and approx. 6% of methyl[2-[p[2,2-bis(ethoxycarbonyl)vinyl]phenoxy]-1-methyleneethyl] and approx. 1.5% of methyl[3-[p-[2,2-bis(ethoxycarbonyl) vinyl]phenoxy) propenyl) and 0.1 to 0.4% of (methylhydrogen)silylene]] (n ~60) (CAS No. 207 574-74-1)
  2,4,6-tris(diisobutyl 4'-aminobenzalmalonate)-s-triazine or 2,4,6-Tris-(biphenyl)-1,3,5-triazine (e.g. Tinosorb A2B sold by BASF),
  2,2'-[6-(4-methoxyphenyl)-1,3,5-triazine-2,4-diyl]bis[5-(2-ethylhexyl)oxy]-phenol (e.g. Tinosorb S sold by BASF),
  N2,N4-bis[4-[5-(1,1-dimethylpropyl)-2-benzoxazolyl] phenyl]-N-6-(2-ethylhexyl)-1,3,5-triazin-2,4,6-triamin (e.g. Uvasorb K 2A sold by Sigma 3V),
  menthyl anthranilate (e.g. Neo Heliopan MA sold by Symrise),
  ethylhexyldimethoxybenzylidenedioxoimidazoline propionate,
  polysilicone-15 (e.g. Parsol SLX sold by Hoffmann LaRoche),
  1,1-dicarboxy(2,2'-dimethylpropyl)-4,4-diphenylbutadiene,
  2,4-bis[5-(1-dimethylpropyl)benzoxazol-2-yl(4-phenyl) imino]-6-(2-ethylhexyl)imino-1,3,5-triazine (e.g. Uvasorb K2A sold by Sigma 3V).

Further suitable UV filters are piperzine derivatives, e.g. the compound of the following structure

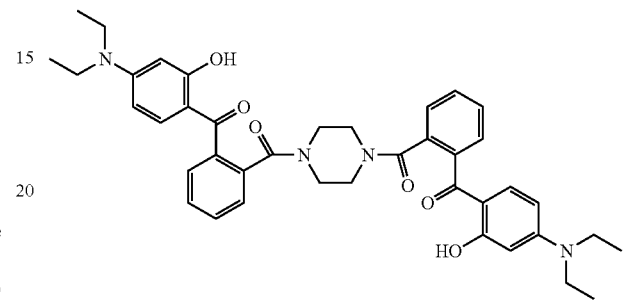

or the UV filters of the following structures:

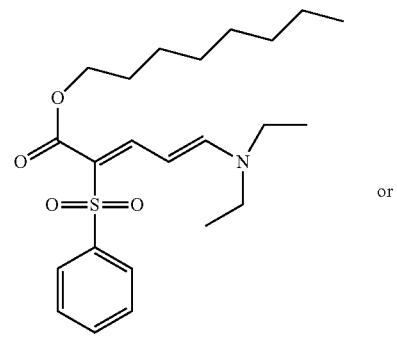

or

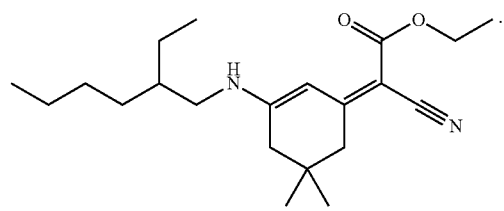

The compounds mentioned in the list should only be regarded as examples. It is of course also possible to use other UV filters.

According to the present invention particularly preferred UV filters are selected from 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and the potassium, sodium and triethanolamine salts thereof.

Preferred capsules may also comprise compounds of the formula I

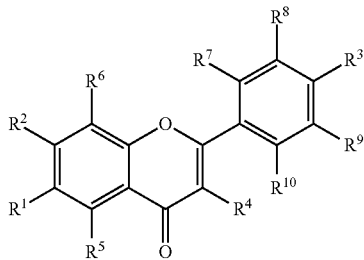

where $R^1$ and $R^2$ are selected from
H
and $OR^{11}$, where $OR^{11}$, independently of one another, stands for
OH
straight-chain or branched $C_1$- to $C_{20}$-alkoxy groups,
straight-chain or branched $C_3$- to $C_{20}$-alkenyloxy groups,
straight-chain or branched $C_1$- to $C_{20}$-hydroxyalkoxy groups, where the hydroxyl group(s) may be bonded to primary or secondary carbon atoms of the chain and furthermore the alkyl chain may also be interrupted by oxygen, and/or
$C_3$- to $C_{10}$-cycloalkoxy groups and/or $C_3$- to $C_{12}$-cyclo-alkenyloxy groups, where the rings may each also be bridged by —$(CH_2)_n$— groups, where n=1 to 3, and/or
mono- and/or oligoglycosyl radicals,
with the proviso that at least one radical from $R^1$ and $R^2$ stands for $OR^{11}$,
and $R^3$ stands for a radical $OR^{11}$ and
$R^4$ to $R^7$ and $R^{10}$ may be identical or different and, independently of one another, stand for
H
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary car-bon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3, and
$R^8$ and $R^9$ may be identical or different and, independently of one another, stand for
H
$OR^{11}$
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary car-bon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3.

The flavonoids of the formula I to be employed in accordance with the invention include broad-band UV filters, other likewise preferred compounds of the formula I exhibit an absorption maximum in the boundary region between UV-B and UV-A radiation. As UV-A-II filters, they therefore advantageously supplement the absorption spectrum of commercially available UV-B and UV-A-I filters. Preferred capsules according to the invention comprise at least one compound of the formula I, where $R^3$ stands for
OH or
straight-chain or branched $C_1$- to $C_{20}$-alkoxy groups, preferably methoxy, ethoxy or ethylhexyloxy, or
mono- and/or oligoglycosyl radicals, preferably glucosyl radicals, and
$R^1$ and/or $R^2$ preferably stand for
OH or
straight-chain or branched $C_1$- to $C_{20}$-alkoxy groups, preferably methoxy, ethoxy or ethylhexyloxy, or
mono- and/or oligoglycosyl radicals, preferably glucosyl radicals.

These preferred compounds are distinguished by particularly intense UV absorption. It has been found that the intensity of the UV absorption is high, in particular, if $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy.

The above-mentioned UV filters may be present alone in the capsules, but mixtures of a plurality of the UV filters mentioned may also be present in the capsules. In addition, the UV filters in the capsules may also be combined with further substances, such as, for example, photostabilisers, cosmetic oils and/or antioxidants, in order to achieve an increase in the stability of the said UV filters. Examples and preferred compounds for the further substances mentioned above, in particular for the photostabilisers, are found in the remainder of this application under the general description of these substances. Examples of suitable cosmetic oils are mineral oils, mineral waxes, oils, such as triglycerides of capric or caprylic acid, furthermore natural oils, such as, for example, castor oil; fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids, silicone oils, such as, for example, dimethylpolysiloxanes, diethylpolysiloxanes, diphenylpolysiloxanes and mixed forms thereof.

Typically, the content of the one or more UV filters in the sol-gel capsule is around 40%.

In general, the nature of the sol-gel capsules employed according to the present invention is not limited, i.e. all sol-gel capsules and matrices can be treated as disclosed in the present invention.

For example, commercially available UV filter capsules can be treated according to the present invention. Examples are Eusolex® UV-Pearls OMC, Eusolex® UV-Pearls 2292, Eusolex® UV-Pearls OB-S or Eusolex® UV-Pearls B-O sold by Merck KGaA, Darmstadt. Further examples are Silasoma® ME and Silasoma® MEA sold by Seiwa Kasei.

According to the present invention, the inorganic material with which the sol-gel capsules are treated is preferably selected from the group consisting of $SiO_2$, $TiO_2$, ZnO and/or $SnO_2$, particularly preferred from $SiO_2$ and/or $TiO_2$.

In a very particularly preferred embodiment of the present invention the inorganic material is $SiO_2$.

In another very particularly preferred embodiment of the present invention the inorganic material is $TiO_2$.

The sol-gel capsules may as well be treated with a mixture of more than one compound selected from the above-defined group.

In step b) of the process of the present invention one or more water-soluble inorganic precursor compounds are added to the suspension of sol-gel capsules. Typically, the precursor compounds are added dissolved in water. Suitable concentrations of these solutions can easily be determined by a person skilled in the art.

The one or more water-soluble inorganic precursor compounds used in step b) are selected according to the inorganic material which is desired to be present on the treated sol-gel capsules. This selection can easily be accomplished by a person skilled in the art.

A suitable precursor compound for the treatment with $SiO_2$ can, e.g., be selected from $Na_2SiO_3$ and $K_2SiO_3$. Preferably, $Na_2SiO_3$ (water glass) is used.

A suitable precursor compound for the treatment with $TiO_2$ can, e.g., be selected from the group consisting of $TiCl_4$ and $TiOSO_4$. Preferably, $TiCl_4$ is used.

A suitable precursor compound for $SnO_2$ is e.g. $SnCl_4$.

Suitable precursor compounds for ZnO are, e.g., $ZnCl_2$ and $ZnSO_4$. Preferably, $ZnCl_2$ is used.

Preferred precursor compounds are, therefore, of $Na_2SiO_3$, $TiCl_4$, $ZnCl_2$ and/or $SnCl_4$ In a preferred embodiment of the present invention an acid or base is added in step b) of the treating process. The addition of an acid or base allows to control and keep constant the pH value during the reaction. The acid or base is selected according to the employed precursor compound.

A typical acid which can be used is hydrochloric acid (HCl). Preferably, HCl is used if $Na_2SiO_3$ is used as precursor compound.

Typical bases which can be used are NaOH, KOH, $NaHCO_3$ and $Na_2CO_3$ in solid form or in aqueous solution. Preferably, NaOH is used if $TiCl_4$, $ZnCl_2$ or $SnCl_4$ is used as precursor compound.

In step c) of the process of the present invention the inorganic material is precipitated onto the capsules' surfaces. This precipitation reaction is a neutralizing reaction.

As mentioned above, the addition of a suitable acid or base allows to control and keep constant the pH value during the precipitation reaction. The pH of step c) is preferably between 1 and 9. Generally, the preferred pH is selected according to the inorganic material compound. If $SiO_2$ is to be deposited on the sol-gel capsules, the pH is preferably between 4 and 9, particularly preferably between 6.5 and 8.5, very particular preferably around 7.2. If $TiO_2$, ZnO or $SnO_2$ is precipitated on the sol-gel capsules, the pH is preferably between 1 and 4, particularly preferably between 1.5 and 3 and very particular preferably around 2.0.

The temperature in step b) and c) is typically between 30 and 120° C., preferably between 50 and 100° C., particularly preferably between 60 and 90° C. and very particular preferably around 75° C.

During an appropriate reaction time the mixture can also be warmed or cooled or the pH can also be modified.

The layer thickness of the inorganic material precipitated onto the surfaces of the sol-gel capsules can be controlled by the amount of inorganic precursor compounds employed. In general, the thickness of the layer of inorganic material on the sol-gel capsules is not limited.

If the capsules are treated with $SiO_2$ the layer thickness of the precipitated $SiO_2$ layer is preferably equal to or greater than 40 nm, more preferably equal to or greater than 70 nm. The total $SiO_2$ layer thickness of the sol-gel capsule (i.e. the capsule wall formed in the sol-gel process and the $SiO_2$ deposited in the treatment process) is preferably between 80 and 120 nm, most preferably between 90 and 110 nm.

If the capsules are treated with $TiO_2$ the layer thickness is preferably equal to or greater than 15 nm, more preferably equal to or greater than 25 nm. Most preferably, the layer thickness is around 30 nm. These preferred dimensions of layer thickness provide improved skin feeling and good UV absorption properties.

The following reaction schemes represent typical chemical reactions taking place during steps b) and c) of the treatment process of the sol-gel capsules with $SiO_2$ and $TiO_2$:

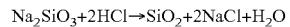

$$Na_2SiO_3 + 2HCl \rightarrow SiO_2 + 2NaCl + H_2O$$

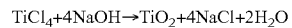

$$TiCl_4 + 4NaOH \rightarrow TiO_2 + 4NaCl + 2H_2O$$

Optionally, steps b) and c) of the process of the present invention can be repeated one or more times corresponding to step d). If steps b) and c) are repeated, the precipitated inorganic material can be the same or different from the inorganic material precipitated in the preceding steps.

For example, the sol-gel capsules may be treated:
twice with $SiO_2$,
first with $SiO_2$, followed by $TiO_2$ or
first with $SiO_2$, followed by $SnO_2$, followed by $TiO_2$.

In a particularly preferred embodiment of the present invention the sol-gel capsules are treated with $SiO_2$ followed by the treatment with $SnO_2$ and/or followed by the treatment with $TiO_2$. In a very particularly preferred embodiment the sol-gel capsules are first treated with $SiO_2$, followed by the treatment with $SnO_2$ and followed by the treatment with $TiO_2$.

Finally, in step e) the treated sol-gel capsules can optionally be isolated and/or dryed in order to obtain a powder.

The isolation of the sol-gel capsules can be accomplished by means which are familiar to the person skilled in the art. For example, they can be centrifuged or filtered. Drying can e.g. be accomplished by spray drying or be heating in an oven. Typically drying temperatures are between 70 and 100° C., preferably between 80 and 95° C., more preferably around 90° C.

In general, a suspension or powder comprising the sol-gel capsules according to the present invention in a form as can be employed directly in cosmetic or dermatological compositions is obtained after step c) or e). Re-suspension of the isolated capsules in, for example, deionised water or in another medium is also conceivable and can be used for use in the compositions according to the invention.

In a preferred embodiment of the present invention the capsules are dried in order to obtain a powder.

The process of the present invention has many advantages:

The use of water glass for treating silica sol-gel capsules allows the preparation of sol-gel capsules exhibiting very robust $SiO_2$ shells. Especially the preparation of a dry powder of capsules is facilitated since the leak tightness of the capsules is increased. These optimal characteristics of the treated sol-gel capsules can for example be achieved if the $SiO_2$ shells exhibit preferably at least 100 nm of thickness.

The treatment of sol-gel capsules with $TiO_2$ results in the fixation of nanoparticulate $TiO_2$ on the surface of the sol-gel capsules avoiding the presence of free $TiO_2$ nanoparticles suspected of being harmful for the human body. Therefore, if the sol-gel capsules comprise one or more UV filters, the treatment with $TiO_2$ allows the preparation of hybrid UV-filters, e.g. $TiO_2$ coated sol-gel capsules comprising encapsulated organic UV filters. The UV protection properties of organic UV filters and inorganic $TiO_2$ can be combined in this way.

A further aspect of the present invention are sol-gel capsules comprising a cosmetic or pharmaceutical active material produced by a process as described above.

A further aspect of the present invention is a formulation comprising sol-gel capsules comprising a cosmetic or pharmaceutical active material produced by a process as described above.

The formulations can be pre-dispersions which are on the one hand themselves directly suitable as cosmetic or dermatological composition and on the other hand can simplify the preparation of such compositions.

In accordance with the invention, the preparation of cosmetic or dermatological compositions comprising capsules according to the invention can therefore be carried out in various ways:

One process for the preparation of a cosmetic or dermatological composition is characterised in that the dryed sol-gel capsules according to the invention are mixed with further ingredients.

A further process for the preparation of a cosmetic or dermatological composition is characterised in that a pre-dispersion as described above is mixed with further ingredients.

The sol-gel capsules are preferably present here in formulations according to the invention in such amounts which ensure that the encapsulated cosmetical or pharmaceutical active material is present in effective amounts in the formulation. Typically, a formulation comprises 5 to 80% by weight of the sol-gel capsules as disclosed above, particularly preferably 30 to 50% by weight of capsules.

The compositions are typically topical compositions, e.g. cosmetic or dermatological compositions or medical devices.

For the purposes of the invention, the term composition is used synonymously with the term formulation.

The composition may include or comprise, essentially consist of or consist of the said requisite or optional constituents or ingredients. All compounds or components which can be used in the compositions are either known and commercially available or can be synthesised by known processes or processes described here.

Furthermore, the compositions according to the invention may also comprise dyes and coloured pigments. The substrates and number and composition of the coating layers of the dyes and coloured pigments are not limited. Preferably, a coloured pigment is of skin or brownish color when used in an amount of 0.5 to 5% by weight. A person skilled in the art is able to easily select a suitable pigment.

Particular preference is given in accordance with the invention to the preparation of cosmetic and dermatological compositions which are in the form of a sunscreen. These may advantageously additionally comprise at least one UV filter and/or at least one inorganic pigment.

Organic UV filters can hereby be selected from the UV filters disclosed above.

These organic UV filters are generally incorporated into cosmetic formulations in an amount of 0.01 to 20 percent by weight, preferably 1-10% by weight.

All the organic UV filters mentioned can also be employed in encapsulated form, in which case the encapsulation techniques described above can be employed. In accordance with the invention, the UV light-protection filters described here can in each case be used alone or naturally also in combination, which is preferred, in sunscreens. They can be combined with UV-B/A chromophores, for example all filters approved and known worldwide, for improving the protective performance (SPF boost) through synergistic effects. They can preferably be employed in combination both with inorganic and with organic UV-A and UV-B filters or mixtures thereof. In addition, the compositions may comprise at least one inorganic UV filter, so-called particular UV filters.

Conceivable as inorganic UV filters are those from the group of titanium dioxides, such as, for example, coated titanium dioxide (e.g. Eusolex® T-2000, Eusolex® T-AQUA, Eusolex®T-AVO, Eusolex®T-OLEO), zinc oxides (e.g. Sachtotee), iron oxides and also cerium oxides or zirconium oxides.

These inorganic UV filters are generally incorporated into cosmetic formulations in an amount of from 0.5 to 20% by weight, preferably 2-10%.

In addition, combinations with pigmentary titanium dioxide or zinc oxide are possible, wherein the particle size of these pigments is at least 200 nm, e.g. Hombitan® FG or Hombitan® FF-Pharma.

Furthermore it can be advantageous if the compositions comprise inorganic UV filters, which have been post-treated with conventional methods, e.g. as disclosed in Cosmetics & Toiletries, February 1990, Vol. 105, pp. 53 64. The post-treating components may here be selected from: amino acids, bees wax, fatty acids, fatty acid alcohols, anionic tensids, lecithine, phospholipids, sodium-, potassium-, zinc-, ferric- or aluminium salts of fatty acids, polyethylene, silicone, proteins (especially collagene or elastine), alkanolamine, silicon dioxide, aluminium dioxide, other metal oxides, phosphates or glycerine.

Preferably used particulate UV filters are:
untreated titanium dioxides, e.g. Microtitanium Dioxide MT 500 B (Tayca); Titandioxd P25 (Degussa),
post-treated micronised titanium dioxides with aluminium oxid and silicon dioxide post-treatment, e.g. Microtitanium Dioxide MT 100 SA (Tayca); Tioveil Fin (Uniqema),
post-treated micronised titanium dioxides with aluminium oxide and/or aluminiumstearate/laurate post-treatment, e.g. Microtitanium Dioxide MT 100 T (Tayca), Eusolex T-2000 (Merck),
post-treated micronised titanium dioxides with ferric oxide and/or ferric stearate post-treatment, e.g. Microtitanium Dioxide MT 100 F (Tayca),
post-treated micronised titanium dioxides with silicon dioxide, aluminium oxid and silicon post-treatment, e.g. Microtitanium Dioxide MT 100 SAS (Tayca),
post-treated micronised titanium dioxides with sodium hexametaphosphate, e.g. Microtitanium Dioxide MT 150 W (Tayca).

The micronised titanium dioxides may as well be post-treated with:
Octyltrimethoxysilane; e.g. Tego Sun T 805 (Degussa),
Silicondioxide; e.g. Parsol T-X (DSM),
Aluminiumoxide and stearic acid; e.g. UV-Titan M160 (Sachtleben),
Aluminium and glycerine; e.g. UV-Titan (Sachtleben),
Aluminium and silikon oils, e.g. UV-Titan M262 (Sachtleben),
sodium hexamethaphosphat and polyvinylpyrrolidon,
polydimethylsiloxane, e.g. 70250 Cardre UF TiO2SI3 (Cardre),
polydimethylhydrogensiloxane, e.g. Microtitanium Dioxide USP Grade Hydrophobic (Color Techniques).

In addition, the combination with the following products may be advantageous:

untreated zinc oxides, e.g. Z-Cote (BASF (Sunsmart)), Nanox (Elementis)

post-treated zinc oxides, e.g. the following products:
  Zinc Oxide CS-5 (Toshibi) (ZnO post-treated with polymethylhydrogenosiloxane)
  Nanogard Zinc Oxide FN (Nanophase Technologies)
  SPD-Z1 (Shin-Etsu) (ZnO post-treated with a silicon grafted acrylpolymer, dispersed in cyclodimethyl siloxane
  Escalol Z100 (ISP) (ZnO post-treated with aluminiumoxide dispersed in a mixture of ethylhexyl methoxycinnamate/PVP-hexadecene/methicone copolymer)
  Fuji ZNO-SMS-10 (Fuji Pigment) (ZnO post-treated with silicon dioxid and polymethylsilesquioxan);
  Untreated ceroxide micropigment e.g. Colloidal Cerium Oxide (Rhone Poulenc)
  Untreated and/or post-treated ferric oxides, e.g. Nanogar (Arnaud).

For example, mixtures of various metal oxides can be used as well, e.g. titanium dioxide and ceroxide with and without post-treatment, e.g. Sunveil A (Ikeda). In addition, mixtures of aluminiumoxide, silicon dioxide and silicon post-treated mixtures of titaniumdioxide, zincoxide, e.g. UV-Titan M261 (Sachtleben) can be used.

These inorganic UV filters are usually incorporated into cosmetic formulations in an amount of from 0.1 to 25% by weight, preferably 2-10%.

By combining two or more compounds listed above it is possible to optimize the protective action against harmful effects of UV radiation.

All of the UV filters specified can be used in encapsulated or in immobilized form as described above.

Besides the compounds described here, the compositions according to the invention may also comprise at least one photostabiliser, preferably con-forming to the formula I

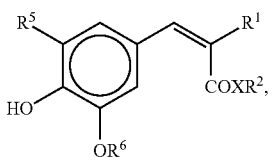

where
$R^1$ is selected from —C(O)CH$_3$, —CO$_2$R$^3$, —C(O)NH$_2$ and —C(O)N(R$^4$)$_2$;
X is O or NH,
$R^2$ is a linear or branched C$_{1\text{-}30}$-alkyl radical;
$R^3$ is a linear or branched C$_{1\text{-}20}$-alkyl radical,
all $R^4$, independently of one another, are H or linear or branched C$_{1\text{-}8}$-alkyl radicals,
$R^5$ is H, a linear or branched C$_{1\text{-}8}$-alkyl radical or a linear or branched —O—C$_{1\text{-}8}$-alkyl radical, and
$R^6$ is a C$_{1\text{-}8}$-alkyl radical,
where the photostabiliser is particularly preferably bis(2-ethylhexyl) 2-(4-hydroxy-3,5-di methoxybenzylidene)malonate. Corresponding photo-stabilisers and their preparation and use are described in International patent application WO 03/007906, the disclosure content of which expressly also belongs to the subject-matter of the present application.

In a further, likewise preferred embodiment of the present invention, the composition according to the invention comprises at least one self-tanning agent.

Advantageous self-tanning agents which can be employed are, inter alia: 1,3-dihydroxyacetone (DHA), glycerolaldehyde, hydroxymethylglyoxal, γ-dialdehyde, erythrulose, 6-aldo-D-fructose, ninhydrin, of 5-hydroxy-1,4-naphthoquinone (juglone) or 2-hydroxy-1,4-naphthoquinone (lawsone) Particularly preferred is 1,3-dihydroxyacetone, erythrulose or their combination.

The preparations according to the invention may in addition comprise further cosmetically active compounds, such as antioxidants, anti-ageing active compounds, anti-wrinkle active compounds, anti-dandruff active compounds, anti-acne, deodorants, anticellulite active compounds, self-tanning substances, skin-lightening substances or vitamins. Skin-protecting or skin-care active compounds can in principle be all active compounds known to the person skilled in the art.

It is furthermore possible and advantageous to combine the compositions according to the invention with antioxidants. A protective action against oxidative stress or against the action of free radicals can thus also be achieved.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and hepta-thionine sulfoximine) in very low tolerated doses (for example pmol to μmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA, pentasodium ethylenediamin tetramethylene phosphonate and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004).

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers, I. M. C. M. Rietjens; Free Radical Biology & Medicine 2001, 31(7), 869-881, have investigated the pH dependence of the antioxidant action of hydroxyflavones. Quercetin exhibits the greatest activity amongst the structures investigated over the entire pH range.

Suitable anti-ageing actives, particularly for skin care formulations, are preferably so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are, in particular, substances from the group consisting of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate and proline. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidine-carboxylic acids (such as ectoine and hydroxyectoine), proline, betaine, glutamine, cyclic diphosphoglycerate, N-acetylornithine, trimethylamine N-oxide, di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) and/or dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidine-carboxylic acid) and derivatives thereof.

Additionally, anti-ageing active compounds sold by Merck can be used, such as 5,7-dihydroxy-2-methylchromone (RonaCare®Luremine), Ronacare®Isoquercetin, Ronacare®Tilirosid or Ronacare®Cyclopeptide 5.

The preparations according to the invention may also comprise one or more skin-lightening active compounds. Skin-lightening active compounds can in principle be all active compounds known to the person skilled in the art. Examples of compounds having skin-lightening activity are hydroquinone, kojic acid, arbutin, aloesin, niacineamide, ascorbic acid, Emblica and rucinol.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vita-min $D_2$), vitamin E, DL-α-tocopherol, tocopherol E acetate, tocopherol hydrogensuccinate, vitamin $K_1$, esculin (vitamin P active ingredient), thia-mine (vitamin $B_1$), nicotinic acid (niacin), pyridoxine, pyridoxal, pyridox-amine (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin.

The retionods described above are as well effective anti-cellulite active agents. Another known anti-cellulite active agent is caffeine.

The compositions according to the invention can be prepared here with the aid of techniques which are well known to the person skilled in the art.

The cosmetic or dermatological composition according to the invention may exist in various forms. Thus, use forms of the preparations according to the invention can, for example, be solutions, suspensions, emulsions or microemulsion of the water-in-oil (W/O) type or of the oil-in-water (O/W) type, a multiple emulsion, for example of the water-in-oil-in-water (W/O/W) type, PIT emulsions, pastes, ointments, gels, creams, lotions, powders, soaps, surfactant-containing cleansing preparations, oils, aerosols, ointments and sprays. Examples of other use forms are solid sticks, shampoos and shower preparations. Any desired customary vehicles, assistants and, if desired, further active compounds may be added to the preparation.

Preferred assistants originate from the group of the preservatives, stabilisers, solubilisers, colorants, i.e. pigments or dyes, or odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic use forms are also powder, emulsion and wax make-up, and sunscreen, pre-sun and after-sun preparations.

The preferred preparation forms according to the invention include, in particular, emulsions and powders.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
 mineral oils, mineral waxes;
 oils, such as triglycerides of capric or caprylic acid, furthermore natural oils, such as, for example, castor oil;
 fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
 silicone oils, such as dimethylpolysiloxanes, diethylpolysiloxanes, di-phenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and waxes, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24 C atoms, in particular 12-18 C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the preparations according to the invention comprise hydrophilic surfactants.

The hydrophilic surfactants are preferably selected from the group of the alkylglucosides, acyl lactylates, betaines and coconut amphoacetates.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS 10 (Seppic).

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols).

It is furthermore advantageous to select the fatty acid ethoxylates from the following group:
polyethylene glycol (20) stearate, polyethylene glycol (21) stearate, poly-ethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethyl-ene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:
fatty alcohols having 8 to 30 C atoms, monoglycerol esters of saturated and/or unsaturated, branched and/or unbranched alkanecarboxylic acids having a chain length of 8 to 24 C atoms, in particular 12-18 C atoms, di-glycerol esters of saturated and/or unsaturated, branched and/or unbranched alkanecarboxylic acids having a chain length of from 8 to 24 C atoms, in particular 12-18 C atoms, monoglycerol ethers of saturated and/or unsaturated, branched and/or unbranched alcohols having a chain length of 8 to 24 C atoms, in particular 12-18 C atoms, diglycerol ethers of saturated and/or unsaturated, branched and/or unbranched alcohols having a chain length of 8 to 24 C atoms, in particular 12-18 C atoms, propylene glycol esters of saturated and/or unsaturated, branched and/or unbranched alkanecarboxylic acids having a chain length of 8 to 24 C atoms, in particular 12-18 C atoms, and sorbitan esters of saturated and/or unsaturated, branched and/or unbranched alkanecarboxylic acids having a chain length of 8 to 24 C atoms, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG 30 dipolyhydroxystearate. The composition may comprise cosmetic adjuvants which are usually used in this type of composition, such as, for example, thickeners, softeners, moisturisers, surfactants, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The preparation according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

A cosmetic composition comprising sol-gel microcapsules comprising UV filters may for example be used to protect the hair against photochemical damage in order to prevent changes of colour shade, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling or treating the hair, in the form of a lotion or gel for brushing or blow-waving the hair, in the form of a hair lacquer, permanent waving composition, colorant or bleach for the hair. The composition having light-protection properties may comprise various adjuvants used in this type of composition, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The compositions according to the invention can be prepared with the aid of techniques which are well known to the person skilled in the art. Even without further comments, it is assumed that a person skilled in the art will be able to utilise the above description in its broadest scope. The following figures and examples are intended to illustrate the present invention without restricting it:

FIGURES

Figure 2:
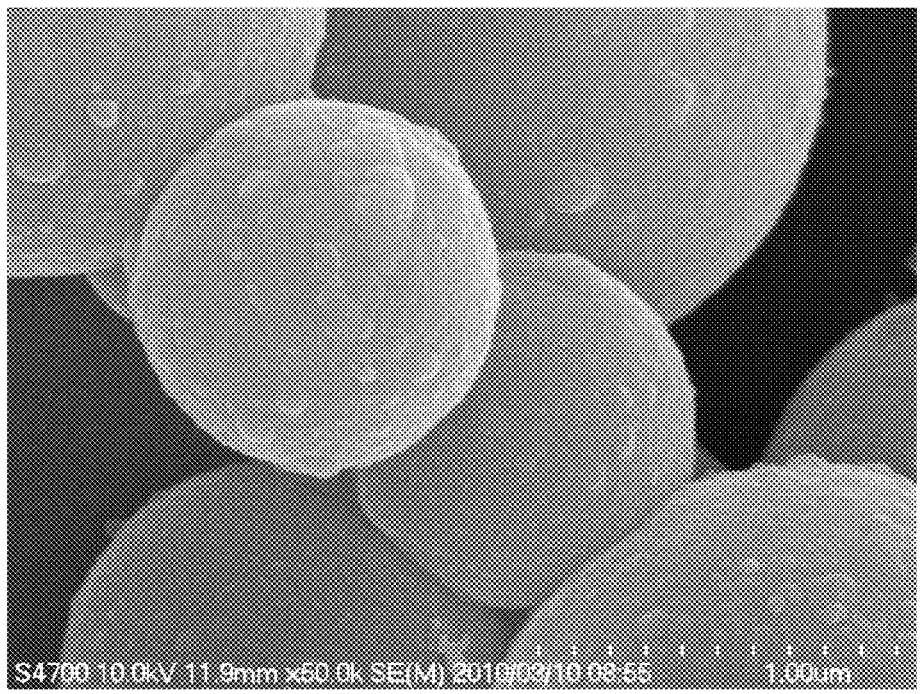
Figure 3:
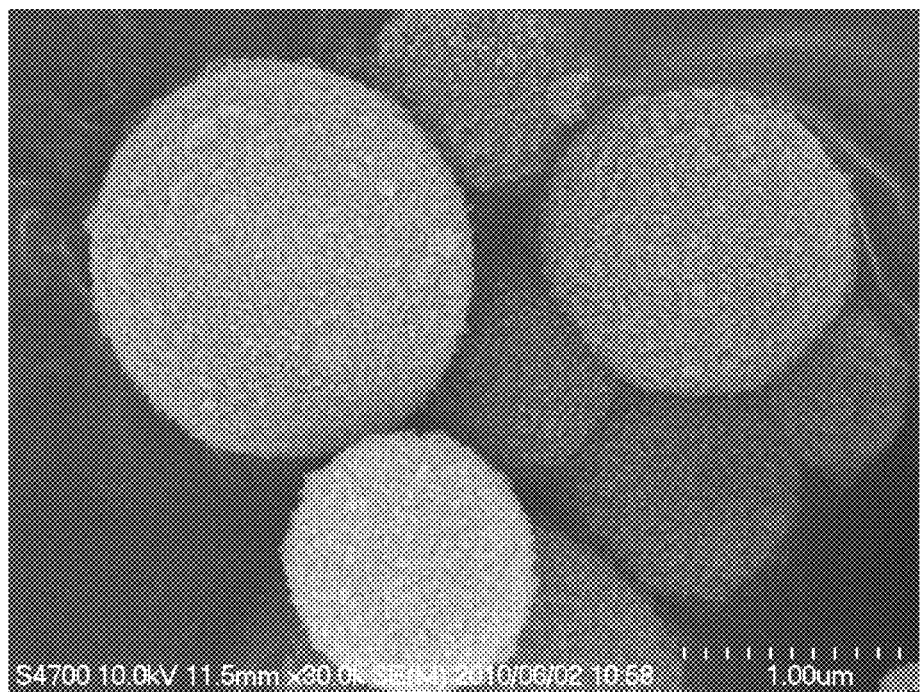
Figure 4:
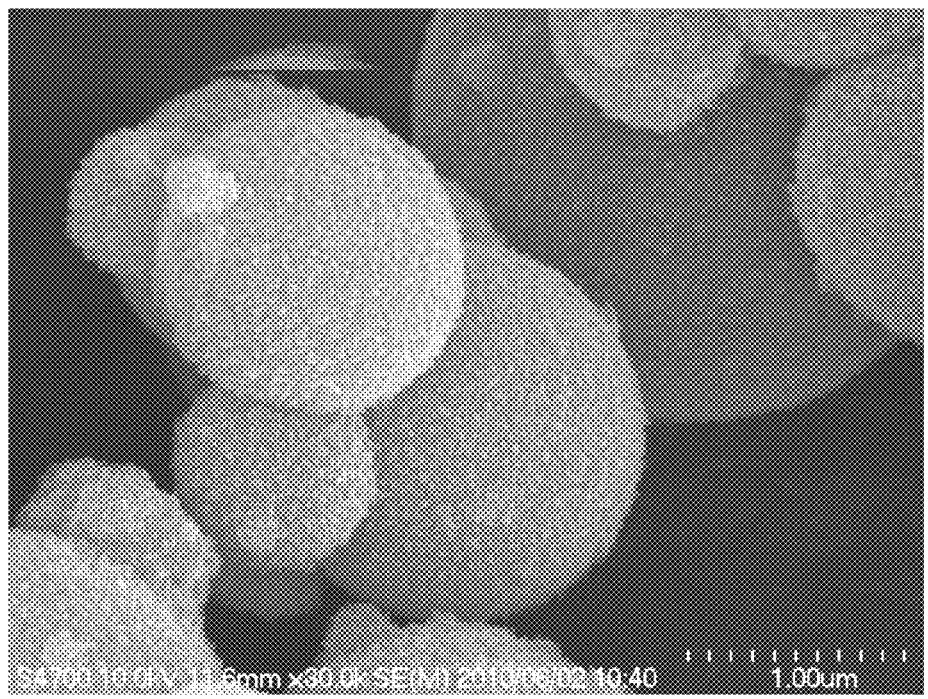
Figure 5:
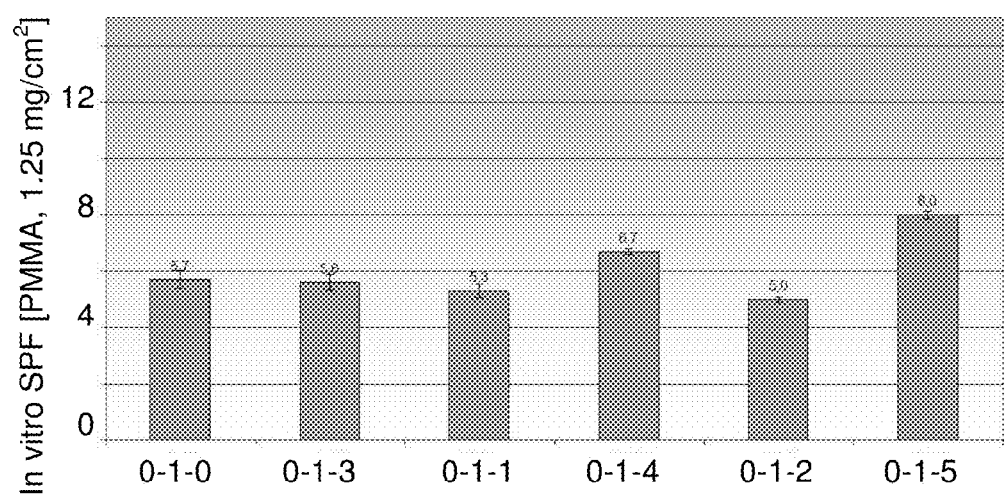
Figure 6:
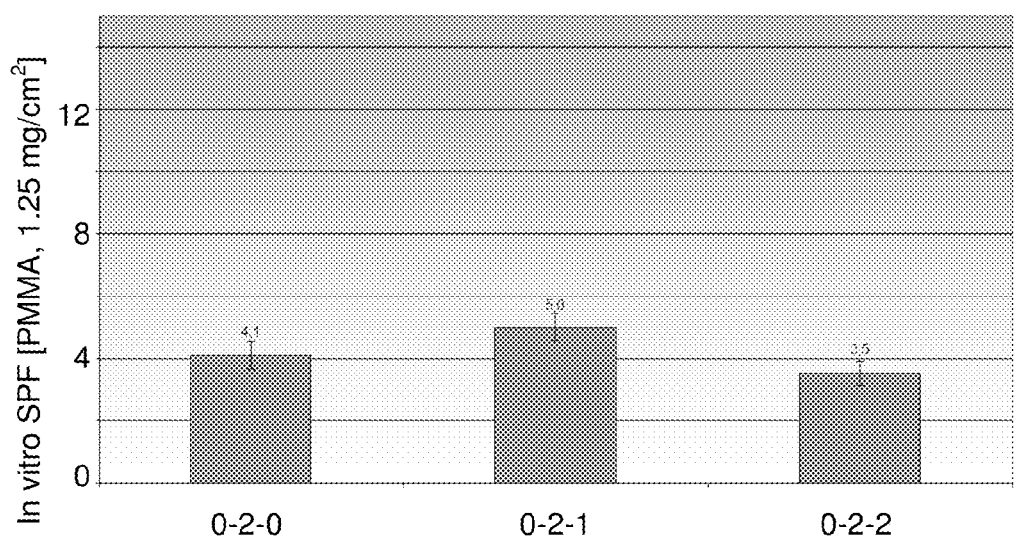
Figure 7:
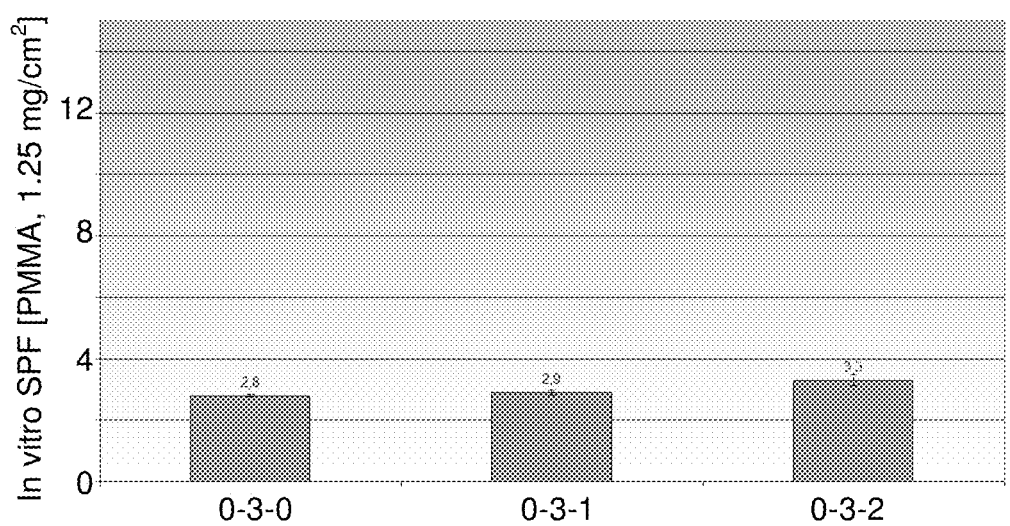
Figure 8:
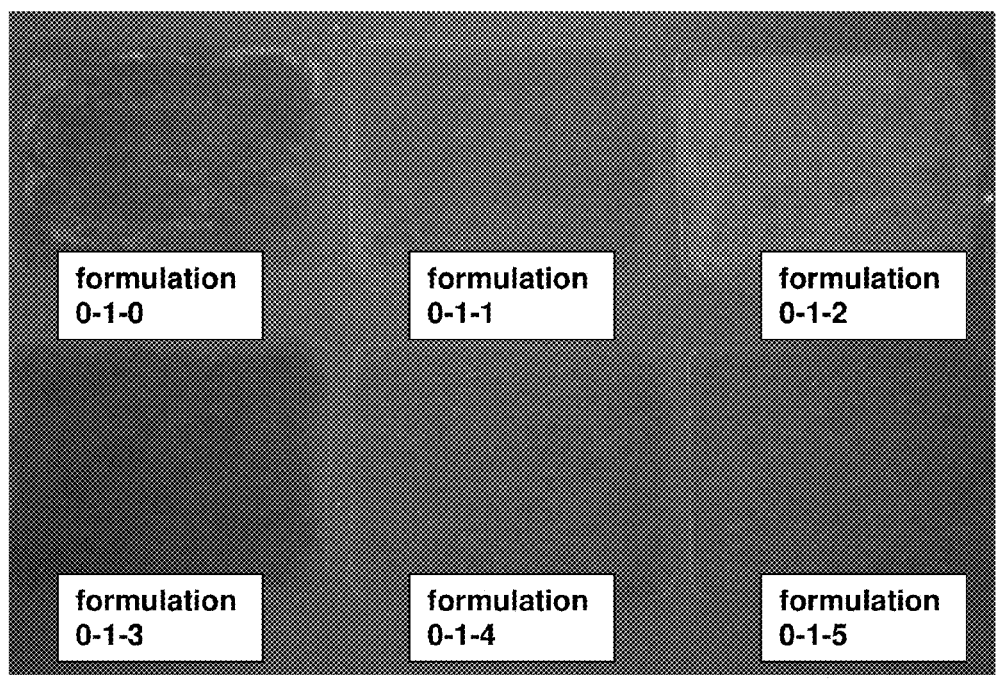
Figure 9:
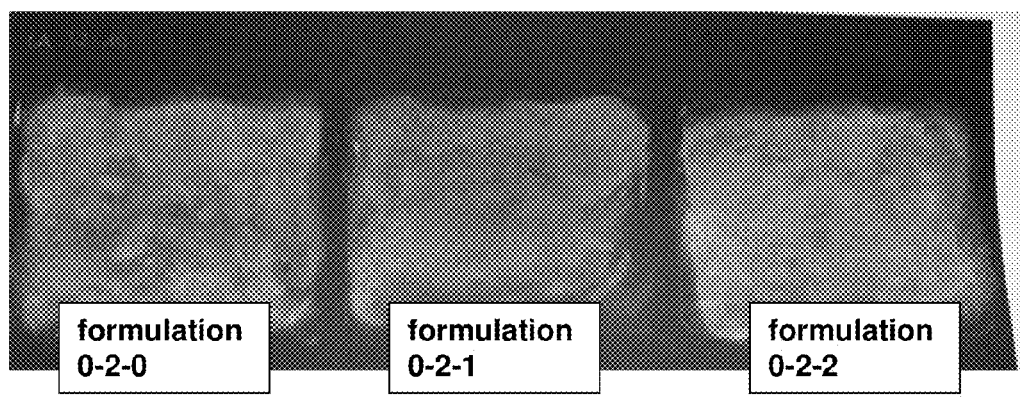
Figure 10:
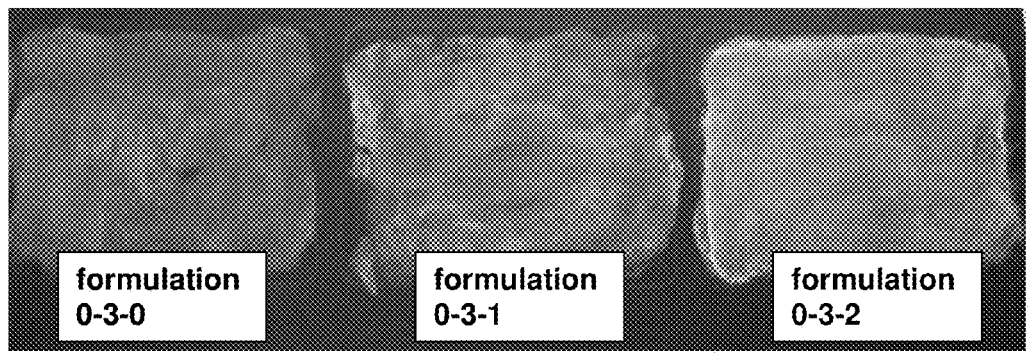
Figure 11:
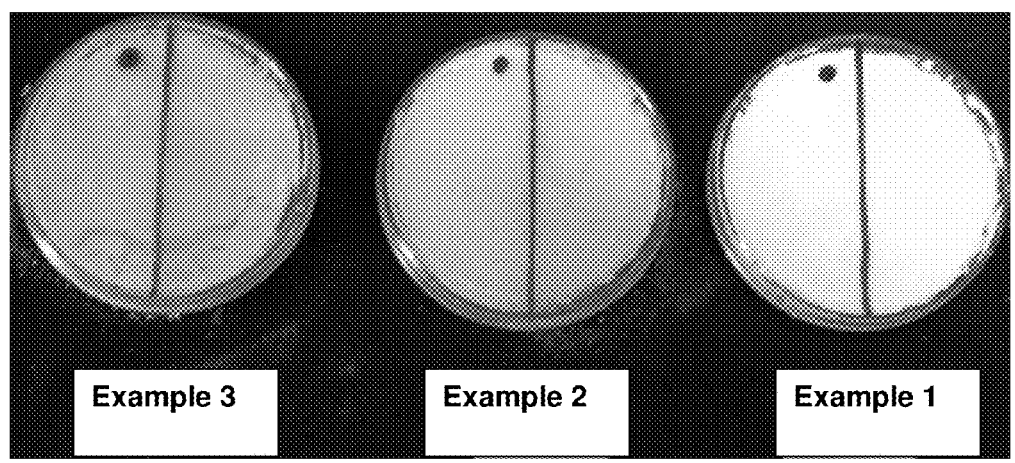
Figure 12A:
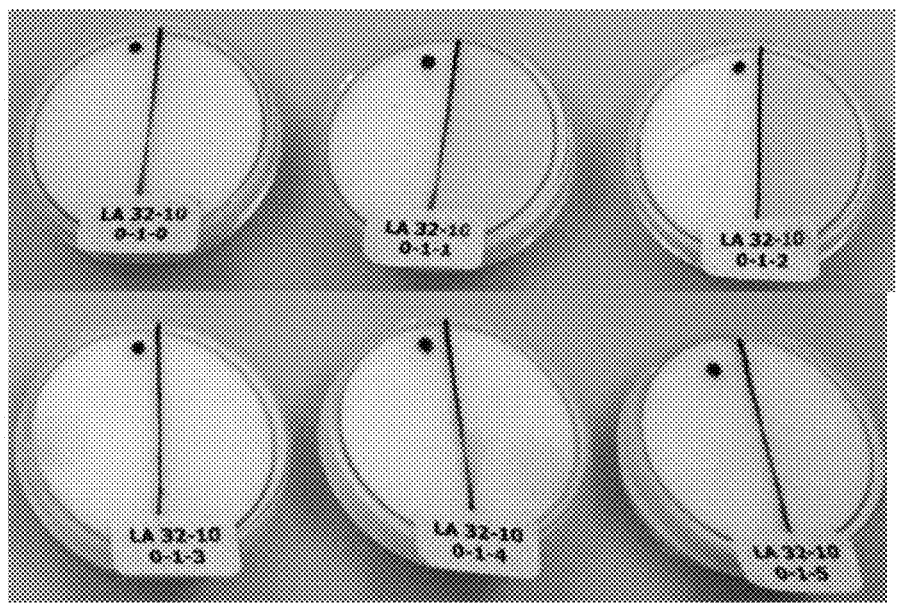
Figure 12B:
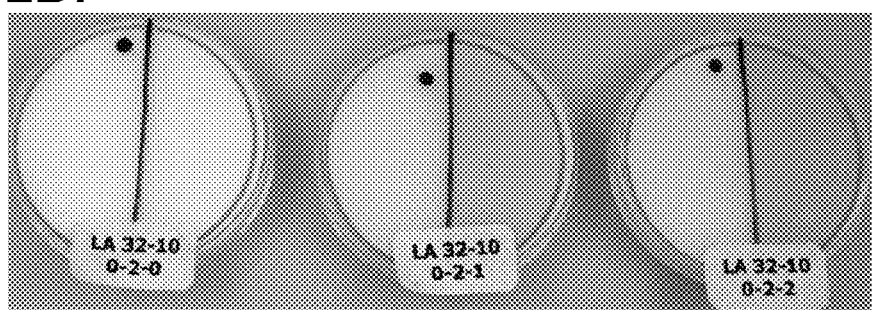
Figure 12C:
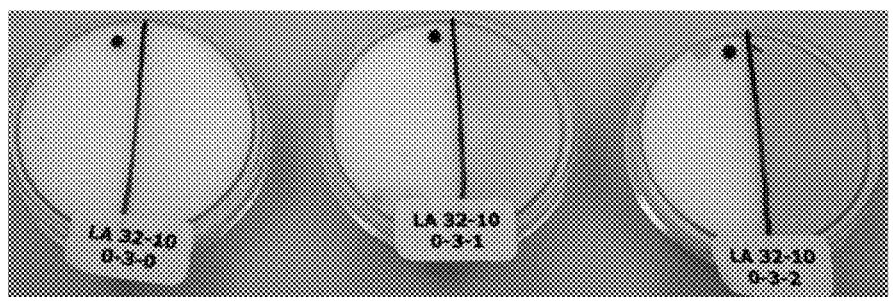

FIGS. 1 to 4 show the SEM photographs of different samples of non-treated and treated Eusolex® UV Pearls OMC. All photos are taken after drying:

FIG. 1: Non-treated sample.
FIG. 2: Sample treated with $SiO_2$ according to Example 1.
FIG. 3: Sample treated with 30 g $TiO_2$ according to Example 2.
FIG. 4: Sample treated with 15 g $TiO_2$ according to Example 3.
FIG. 5 shows the in vitro SPF values of the W/O emulsions according to Example 4: The SPF values of emulsions comprising treated sol-gel capsules according to Examples 1 to 3 (0-1-0, 0-1-1, 0-1-2) are compared with formulations comprising UV filters in non-encapsulated form (0-1-3, 0-1-4, 0-1-5).
FIG. 6 shows the in vitro SPF values of the O/W emulsions according to Example 5: The SPF values of emulsions comprising treated sol-gel capsules according to Examples 1 to 3 are compared.
FIG. 7 shows the in vitro SPF values of the gel formulations according to Example 6: The SPF values of emulsions comprising treated sol-gel capsules according to Examples 1 to 3 are compared.
FIG. 8 shows the whitening effect of the W/O emulsions according to Example 4 on black paper: The whitening effect of emulsions comprising treated sol-gel capsules according to Examples 1 to 3 is compared with formulations comprising UV filters in non-encapsulated form.
FIG. 9 shows the whitening effect of the O/W emulsions according to Example 5 on black paper.
FIG. 10 shows the whitening effect of the gel formulations according to Example 6 on black paper.
FIG. 11 shows the color stability of the three samples according to Examples 1 to 3 under UV-irradiation. The left side of each dish (marked with a dot) shows the non-irradiated sample, whereas the right side of each dish shows the sample after an irradiation of 5 MED (250 kJ/m$^2$).
FIG. 12 shows the color stability of the formulations according to Examples 4, 5 and 6 under UV-irradiation. The left side of each dish (marked with a dot) shows the non-irradiated sample, whereas the right side of each dish shows the sample after an irradiation of 5 MED (250 kJ/m$^2$).
FIG. 12A: Color stability of the formulations according to Example 4. FIG. 12B: Color stability of the formulations according to Example 5. FIG. 12C: Color stability of the formulations according to Example 6.

EXAMPLES

Example 1

Treatment of UV Filter Capsules with $SiO_2$ 135 g of Eusolex® UV-Pearls OMC (OMC=50 g, $SiO_2$=6.75 g; available from Merck KGaA, Darmstadt) is put in a 5 L reactor and adjusted to 2 L with deionized water.

432.5 ml of water glass solution (43.25 g $SiO_2$) is prepared by diluting 80.5 g water glass (26% as $SiO_2$) with water.

100 ml of 10% HCl solution is prepared for pH control (pH=7.2).

The preparation procedure using the above described batch of Eusolex® UV-Pearls OMC is carried out according to the following recipe:

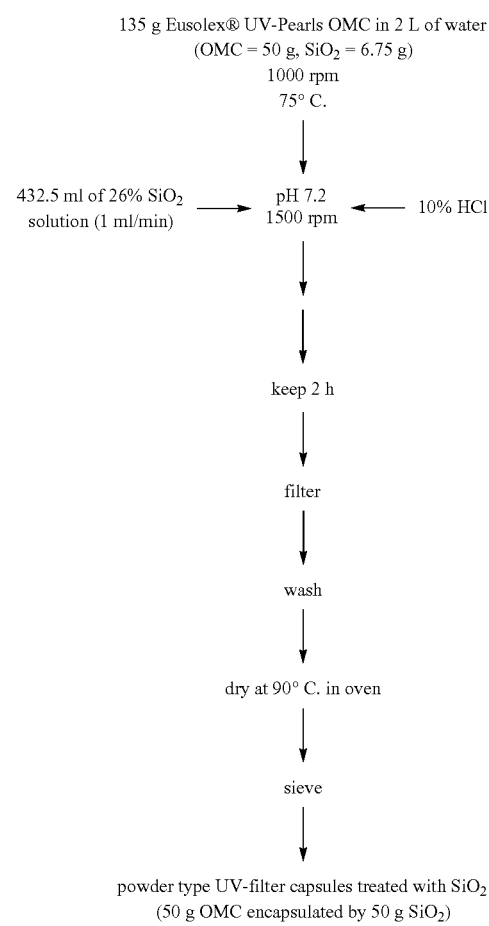

The prepared sample is a well dispersed white powder exhibiting good stability. The shell thickness of $SiO_2$ is calculated around 116 nm. FIG. 2 shows a SEM photograph of the sample.

The color stability of the sample under UV-irradiation is shown in FIG. 11.

Example 2

Treatment of UV Filter Capsules with $SiO_2$, $SnO_2$ and $TiO_2$ 135 g of Eusolex® UV-Pearls OMC(OMC=50 g, $SiO_2$=6.75 g; available from Merck KGaA, Darmstadt) is put in a reactor and adjusted to 2 L with deionized water.

432.5 ml of a water glass solution (43.25 g $SiO_2$) is prepared by diluting 80.5 g water glass (26% as $SiO_2$) with water.

62 ml of a $SnCl_4$ solution ($SnO_2$=2 g) is prepared by dissolving 3.286 g $SnCl_4$ in deionized water.

300 ml of a $TiCl_4$ solution ($TiO_2$=30 g) is prepared corresponding to a concentration of 100 g $TiO_2$/1000 ml.

The preparation procedure using the above described batch of Eusolex® UV-Pearls OMC is carried out according to the following recipe:

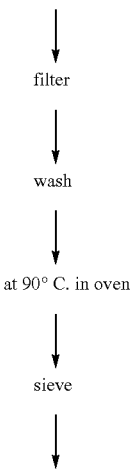

135 g Eusolex® UV-Pearls OMC in 2 L of water
(OMC = 50 g, $SiO_2$ = 6.75 g)
1000 rpm
75° C.
↓
432.5 ml of 26% $SiO_2$ solution (1 ml/min) → pH 7.2, 1500 rpm ← 10%-HCl
↓
keep 2 h
↓
62 ml of $SnCl_4$ solution ($SnO_2$ = 2 g) (1 ml/min) → pH 2.0, 1500 rpm ← 32% NaOH
↓
300 ml of $TiCl_4$ solution ($TiO_2$ = 30 g) (1 ml/min) → pH 2.0, 1500 rpm ← 32% NaOH
↓
pH 5.0
↓
filter
↓
wash
↓
dry at 90° C. in oven
↓
sieve
↓
powder type UV-filter capsules treated with $SiO_2$, $SnO_2$ and $TiO_2$
(30 g $TiO_2$/2 g $SnO_2$/50 g $SiO_2$/50 g OMC)

The prepared sample is a well dispersed white powder exhibiting good stability. The fixed $TiO_2$ layer's thickness is calculated around 40 nm. FIG. 3 shows a SEM photograph of the sample.

The color stability of the sample under UV-irradiation is shown in FIG. 11.

Example 3

Treatment of UV Filter Capsules with $SiO_2$, $SnO_2$ and $TiO_2$

Example 3 is carried out according to the same procedure as described in Example 2 except for the amount of $TiO_2$. Instead of 300 ml only 150 ml of the $TiCl_4$ solution are used. The capsules consist of ca. 15 g $TiO_2$/2 g $SnO_2$/50 g $SiO_2$/50 g OMC.

The prepared sample is a well dispersed white powder exhibiting good stability. The fixed $TiO_2$ layer's thickness is calculated around 20 nm. FIG. 4 shows a SEM photograph of the sample.

The color stability of the sample under UV-irradiation is shown in FIG. 11.

Example 4

Water in Oil Emulsion (W/O) Comprising Treated UV Filter Capsules

The formulation samples 0-1-0, 0-1-1 and 0-1-2 refer to formulations comprising 5% of the treated UV filter capsules of Examples 1 to 3. For comparison, corresponding formulations comprising free UV filters instead of encapsulated UV filters are listed as well (0-1-3, 0-1-4, 0-1-5).

| Ingredient | INCI | 0-1-0 [%] | 0-1-1 [%] | 0-1-2 [%] | 0-1-3 [%] | 0-1-4 [%] | 0-1-5 [%] |
|---|---|---|---|---|---|---|---|
| A | | | | | | | |
| Treated UV-Pearls of Example 1 | | 5.00 | | | | | |
| Treated UV-Pearls of Example 3 | | | 5.00 | | | | |
| Treated UV-Pearls of Example 2 | | | | 5.00 | | | |
| Eusolex 2292 | | | | | 2.50 | 2.13 | 1.90 |

-continued

| Ingredient | INCI | 0-1-0 [%] | 0-1-1 [%] | 0-1-2 [%] | 0-1-3 [%] | 0-1-4 [%] | 0-1-5 [%] |
|---|---|---|---|---|---|---|---|
| Eusolex T-2000 (80% TiO2) | | | | | | 0.81 | 1.41 |
| Abil EM 90 | CETYL PEG/PPG-10/1 DIMETHICONE | 2.50 | 2.50 | 2.50 | 2.50 | 2.50 | 2.50 |
| Abil Wax 9801 | CETYL DIMETHICONE | 1.00 | 1.00 | 1.00 | 1.00 | 1.00 | 1.00 |
| Gilugel SIL 5 | ALUMINIUM/MAGNESIUM HYDROXIDE | 5.00 | 5.00 | 5.00 | 5.00 | 5.00 | 5.00 |
| Paracera W 80 | CERESIN (MICRO-CRYSTALLINE WAX) | 1.00 | 1.00 | 1.00 | 1.00 | 1.00 | 1.00 |
| Cutina HR | HYDROGENATED CASTOR OIL | 1.00 | 1.00 | 1.00 | 1.00 | 1.00 | 1.00 |
| Cetiol AB | C12-15 ALKYL BENZOATE | 5.00 | 5.00 | 5.00 | 5.50 | 5.00 | 5.00 |
| Tegosoft DEC | DIETHYLHEXYL CARBONATE | 5.00 | 5.00 | 5.00 | 6.00 | 6.00 | 6.00 |
| Tegosoft OS | ETHYLHEXYL STEARATE | 2.50 | 2.50 | 2.50 | 2.50 | 2.50 | 2.50 |
| Paraffin (low viscosity) | PARAFFINUM LIQUIDUM (MINERAL OIL) | 2.50 | 2.50 | 2.50 | 2.50 | 2.50 | 2.50 |
| Dow Corning 345 | CYCLOPENTASILOXANE, CICLOHEXAS | 9.00 | 9.00 | 9.00 | 10.00 | 10.00 | 9.50 |
| Prisorine 3505 | ISOSTEARIC ACID | 1.00 | 1.00 | 1.00 | 1.00 | 1.00 | 1.00 |
| all-rac-alpha-Tocopherol acetate | TOCOPHERYL ACETATE | 0.50 | 0.50 | 0.50 | 0.50 | 0.50 | 0.50 |
| B | | | | | | | |
| Glycerin anhydrous | GLYCERIN | 3.00 | 3.00 | 3.00 | 3.00 | 3.00 | 3.00 |
| RonaCare ® Sodium Chloride | SODIUM CHLORIDE | 0.50 | 0.50 | 0.50 | 0.50 | 0.50 | 0.50 |
| Water, demineralized | AQUA (WATER) | 54.50 | 54.50 | 54.50 | 54.50 | 54.56 | 54.69 |
| Sodium hydroxide, 10% | AQUA (WATER), SODIUM HYDROXIDE | 0.00 | 0.00 | 0.00 | 0.00 | 0.00 | 0.00 |
| C | | | | | | | |
| Germaben II | | 1.00 | 1.00 | 1.00 | 1.00 | 1.00 | 1.00 |
| | | 100.00 | 100.00 | 100.00 | 100.00 | 100.00 | 100.00 |

The in vitro SPF values of these formulations are shown in FIG. 5. The whitening effect of these formulations is shown in FIG. 8.

The color stability of the formulations under UV-irradiation is shown in FIG. 12 A.

Example 5

Oil in Water Emulsion (O/W) Comprising Treated UV Filter Capsules

The formulation samples 0-2-0, 0-2-1 and 0-2-2 refer to formulations comprising 10% of the treated UV filter capsules of Examples 1 to 3.

| Ingredient | INCI | 0-2-0 [%] | 0-2-1 [%] | 0-2-2 [%] |
|---|---|---|---|---|
| A | | | | |
| Montanov 202 | ARACHIDYL ALCOHOL, BEHENYL ALCOHOL, ARACHIDYLGLUCOSIDE | 3.00 | 3.00 | 3.00 |
| Lanol 99 | ISONONYL ISONONANOATE | 2.00 | 2.00 | 2.00 |
| Arlamol HD | ISOHEXADECANE | 10.00 | 10.00 | 10.00 |
| Euxyl PE 9020 | PHENOXYETAHNOL, ETHYLHEXYL, GLYCERIN | 1.00 | 1.00 | 1.00 |
| B | | | | |
| Glycerin (87 %) | GLYCERIN, AQUA (WATER) | 3.00 | 3.00 | 3.00 |
| Water, demineralized | AQUA (WATER) | 60.00 | 60.00 | 60.00 |
| RonaCare ® Ectoin | | 2.00 | 2.00 | 2.00 |
| C | | | | |
| Simulgel NS | HYDROXYETHYL ACRYLATE/SODIUM ARCYLOYLDIMETHYL-ALAURATE COPOLYMER, SQUALANE, POLYSORBATE 60 | 2.00 | 2.00 | 2.00 |
| E | | | | |
| Treated UV-Pearls of Example 1 | | 10.0 | | |
| Treated UV-Pearls of Example 3 | | | 10.0 | |
| Treated UV-Pearls of Example 2 | | | | 10.0 |
| | | 100.00 | 100.00 | 100;00 |

The in vitro SPF values of these formulations are shown in FIG. 6.

The whitening effect of these formulations is shown in FIG. 9.

The color stability of the formulations under UV-irradiation is shown in FIG. 12 B.

Example 6

Gel Comprising Treated UV Filter Capsules

The formulation samples 0-3-0, 0-3-1 and 0-3-2 refer to formulations comprising the treated UV filter capsules of Examples 1 to 3.

| Ingredient | INCI | 0-3-0 [%] | 0-3-1 [%] | 0-3-2 [%] |
|---|---|---|---|---|
| A | | | | |
| Treated UV-Pearls of Example 1 | | 5.00 | | |
| Treated UV-Pearls of Example 3 | | | 5.00 | |
| Treated UV-Pearls of Example 2 | | | | 5.00 |
| Carbopol Ultrez 10 | CARBOMER | 0.40 | 0.40 | 0.40 |
| Water, demineralized | AQUA (WATER) | 63.80 | 63.80 | 63.80 |
| B | | | | |
| RonaCare ® Ectoin Tris (hydroxymethyl)-aminomethan | ECTOIN TROMETHAMINE | 0.60 | 0.60 | 0.60 |
| Germaben II | PROPYLENE GLYCOL, DIAZOLIDINYL UREA, ME | 0.20 | 0.20 | 0.20 |
| Water, demineralized | AQUA (WATER) | 10.00 | 10.00 | 10.00 |
| C | | | | |
| Lubrajel DV | PROPYLENE GLYCOL, POLYGLY-CERYLMETHA | 18.00 | 18.00 | 18.00 |
| D | | | | |
| Lubrajel Oil | PVM/MA COPOLYMER, PROPYLENE GLYCOL, | 2.00 | 2.00 | 2.00 |
| | | 100.00 | 100.00 | 100.00 |

The in vitro SPF values of these formulations are shown in FIG. 7.

The whitening effect of these formulations is shown in FIG. 10.

The color stability of the formulations under UV-irradiation is shown in FIG. 12 C.

The invention claimed is:

1. A process for treating sol-gel capsules comprising an encapsulated cosmetic or pharmaceutical active material with an inorganic material, said process comprising the following steps
   a) providing a suspension of sol-gel capsules,
   b) adding one or more water-soluble inorganic precursor compounds,
   c) precipitating the inorganic material onto the capsules' surfaces,
   d) optionally repeating steps b) and c) one or more times, and
   e) optionally isolating and/or drying the treated sol-gel capsules.

2. The process of claim 1, wherein the sol-gel capsules are silica capsules.

3. The process of claim 1, wherein the inorganic material is selected from the group consisting of $SiO_2$, $TiO_2$, ZnO and $SnO_2$.

4. The process of claim 1, wherein the one or more inorganic precursor compounds of step b) are selected from the group consisting of $Na_2SiO_3$, $TiCl_4$, $ZnCl_2$ and $SnCl_4$.

5. The process of claim 1, wherein in step b) an acid or base is added.

6. The process of claim 1, wherein the temperature of step b) and c) are between 30 and 120° C.

7. The process of claim 1, wherein the pH of step c) is between 1 and 9.

8. The process of claim 1, wherein the sol-gel capsules are first treated with $SiO_2$, followed by the treatment with $SnO_2$ and/or followed by the treatment with $TiO_2$.

9. The process of claim 1, wherein the encapsulated cosmetic or pharmaceutical active material comprises one or more UV filters.

10. The process of claim 9, wherein the one or more UV filters are one or more of 3-(4'-methylbenzylidene)-dl-camphor, 1-(4- tert-butylphenyl)-3-(4-methoxyphenyl)propane-1,3-dione, 4-isopropyl-dibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, or 2-phenylbenzimidazole-5-sulfonic acid or a the potassium, sodium or triethanolamine salt thereof.

11. The process of claim 1, wherein the sol-gel capsules in step a) are obtained in a process that comprises the following steps
   a1) preparing an oil-in-water emulsion of a hydrophobic solution comprising the sol-gel precursor and at least one cosmetic or pharmaceutical active material in an aqueous solution,
   b1) mixing the emulsion from step) with another aqueous solution in order to accelerate the condensation polymerisation reaction,
   optionally c1) separating off reaction products from the sol-gel precursor, and isolating the sol-gel capsules.

12. A sol-gel capsule comprising an encapsulated cosmetic or pharmaceutical active material produced by a process, which comprises the following steps
   a) providing a suspension of sol-gel capsules,
   b) adding one or more water-soluble inorganic precursor compounds,
   c) precipitating the inorganic material onto the capsules' surfaces,
   d) optionally repeating steps b) and c) one or more times, and
   e) optionally isolating and/or drying the treated sol-gel capsules.

13. A formulation comprising sol-gel capsules of claim 12 and at least one other ingredient.

14. A formulation of claim 13, which comprises 5 to 80% by weight of sol-gel capsules.

15. A process for the preparation of a formulation, comprising mixing the sol-gel capsules of claim 12 with further ingredients.

16. A sol-gel capsule according to claim 12, which are silica capsules.

17. A sol-gel capsule according to claim 12, wherein the inorganic material is selected from the group consisting of $SiO_2$, $TiO_2$, ZnO and $SnO_2$.

18. A sol-gel capsule according to claim 12, wherein the one or more inorganic precursor compounds of step b) are selected from the group consisting of $Na_2SiO_3$, $TiCl_4$, $ZnCl_2$ and $SnCl_4$.

19. A sol-gel capsule according to claim 12, wherein the sol-gel capsules are first treated with $SiO_2$, followed by the treatment with $SnO_2$ and/ or followed by the treatment with $TiO_2$.

20. A sol-gel capsule according to claim 12, wherein the encapsulated cosmetic or pharmaceutical active material comprises one or more UV filters.

21. A sol-gel capsule according to claim 12, produced by a process that consists essentially of the following steps
 a) providing a suspension of sol-gel capsules,
 b) adding one or more water-soluble inorganic precursor compounds,
 c) precipitating the inorganic material onto the capsules' surfaces,
 d) optionally repeating steps b) and c) one or more times, and
 e) optionally isolating and/or drying the treated sol-gel capsules.

22. A sol-gel capsule according to claim 12, produced by a process that consists of the following steps
 a) providing a suspension of sol-gel capsules,
 b) adding one or more water-soluble inorganic precursor compounds,
 c) precipitating the inorganic material onto the capsules' surfaces,
 d) optionally repeating steps b) and c) one or more times, and
 e) optionally isolating and/or drying the treated sol-gel capsules.

* * * * *